United States Patent [19]

Coughenour et al.

[11] Patent Number: 4,837,226
[45] Date of Patent: Jun. 6, 1989

[54] POLYCYCLIC AMINE DERIVATIVES USEFUL AS CEREBROVASCULAR AGENTS

[75] Inventors: Linda L. Coughenour; Graham Johnson, both of Ann Arbor, Mich.

[73] Assignee: Warner-Lambert Company, Morris Plains, N.J.

[21] Appl. No.: 186,834

[22] Filed: Apr. 27, 1988

[51] Int. Cl.$^4$ .................... C07D 333/76; A61K 31/38
[52] U.S. Cl. .................... 514/443; 514/463; 514/468; 514/656; 549/42; 549/432; 549/458; 549/43; 564/427
[58] Field of Search .................... 549/31, 432, 458, 42, 549/43; 564/308, 427; 514/443, 463, 468, 647, 656, 467

[56] References Cited

U.S. PATENT DOCUMENTS 3,111,527 11/1963 Godefroi .................... 549/43
3,159,677 12/1964 Godefroi et al. .................... 260/501.1
3,206,480 9/1965 Godefroi et al. .................... 549/460
3,987,116 10/1976 Diamond .................... 560/56

FOREIGN PATENT DOCUMENTS 893920 5/1960 United Kingdom .

OTHER PUBLICATIONS

J. Timothy Greenamyre, et al. "Alterations in L-Glutamate Binding in Alzheimer's and Huntington's Diseases", Mar. 22, 1985, vol. 227, pp. 1496-1499.

Primary Examiner—Mary C. Lee
Assistant Examiner—E. Brendan Magrab
Attorney, Agent, or Firm—Elizabeth M. Anderson

[57] ABSTRACT

A method for the treatment of cerebrovascular disorders by administering a fluorenamine, dibenzofuranamine, or dibenzothiophenamine derivative.

11 Claims, No Drawings

POLYCYCLIC AMINE DERIVATIVES USEFUL AS CEREBROVASCULAR AGENTS

BACKGROUND OF THE INVENTION

The present invention covers a series of fluorenamine, dibenzofuranamine and dibenzothiophenamines, derivatives useful in the treatment of cerebrovascular disorders.

U.S. Pat. Nos. 3,159,677, 3,206,480 and 3,111,527 are concerned with fluorenamines, dibenzofuranamines, dibenzothiophenamines and processes for preparing them. The compounds have useful central nervous system depressant activity.

Excessive excitation by neurotransmitters can cause the degeneration and death of neurons. It is believed that this excitotoxic action is mediated by the excitatory amino acids, glutamate and aspartate, acting at the N-methyl-D-aspartate (NMDA) receptor. This action is responsible for neuronal loss in cerebrovascular disorders such as: cerebral ischemia or cerebral infarction resulting from a range of conditions such as thromboembolic or hemorrhagic stroke, cerebral vasospasm, hypoglyceMia, cardiac arrest, status epilepticus, perinatal asphyxia, anoxia such as from drowning, pulmonary surgery and cerebral trauma. Thus the compounds of the instant invention which are active as noncompetitive antagonist of NMDA receptor mediated ion channel activation are useful in the treatment of the above disorders. In addition, by this NMDA antagonist action, the compounds of the instant invention are also useful for treating schizophrenia, epilepsy, spasticity, neurodegenerative disorders such as Alzheimer's disease, or Huntington's disease, Olivo-pontocerebellar atrophy, spinal cord injury, and poisoning by exogenous NMDA poisons (e.g. some forms of lathyrism). Further uses are as analgesics *J. Pharmacol. Exp. Ther.*, 243, 9, (1987) and anesthetics, particularly for use in surgical procedures where a finite risk of cerebrovascular damage exists.

There are no specific therapies for these neurodegenerative disorders, but competitive and non-competitive NMDA antagonists acting specifically to antagonize excitatory neurotransmission at NMDA receptors offer a novel therapeutic approach to these disorders; B. Meldrum in "Neurotoxins and Their Pharmacological Implications" edited by P. Jenner, Raven Press, New York, 1987. Recent literature reports have confirmed the protective action of examples of this class of agents in pharmacological models of neurodegenerative disorders (J. W. Mcdonald, F. S. Silverstein and M. V. Johnston, *Eur. J. Pharmacol.*, 140, 359, (1987); R. Gill, A. C. Foster and G. N. Woodruff, *J. Neurosci.*, 7, 3343, (1987); S. M. Rothman, J. H. Thurston, R. E. Hauhart, G. D. Clark and J. S. Soloman, *Neurosci.*, 21, 673, (1987); M. P. Goldberg, P-C. Pham and D. W. Choi, *Neurosci. Lett.*, 80, 11, (1987).

The present invention provides a method of prevention and/or treatment of the aforementioned pathological conditions by the administration of specific, orally active non-competitive NMDA receptor antagonists.

SUMMARY OF THE INVENTION

The present invention provides a method of treatment for cerebrovascular disorders which comprises specific non-competitive NMDA antagonists of formula

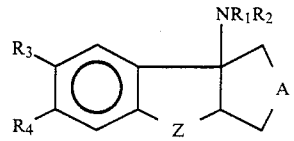

wherein $R_1$–$R_4$, Z and A are defined herein below.

Preferred compounds of the present invention are those
wherein:
Z is methylene or sulfur;
$R_1$ is hydrogen, methyl, ethyl, propyl or $(CH_2)_3OMe$;
$R_2$ is hydrogen or methyl;
$R_3$, $R_4$ are each hydrogen;
A is —$CH_2CH_2$—, —CH=CH— or when Z is methylene, A is additionally —CH(Me)CH$_2$—.

Preferred compounds of the instant invention are:
1,4,9,9a-tetrahydro-4aH-fluoren-4a-amine,
1,4,9,9a-tetrahydro-N-methyl-4aH-fluoren-4a-amine,
1,4,9,9a-tetrahydro-N,N-dimethyl-4aH-fluoren-4a-amine,
N-ethyl-1,4,9,9a-tetrahydro-4aH-fluoren-4a-amine,
1,4,9,9a-tetrahydro-N-propyl-4aH-fluoren-4a-amine,
N-butyl-1,4,9,9a-tetrahydro-4aH-fluoren-4a-amine,
1,4,9,9a-tetrahydro-N-pentyl-4aH-fluoren-4a-amine,
1,4,9,9a-tetrahydro-3-methyl-4aH-fluoren-4a-amine,
1,4,9,9a-tetrahydro-3-methyl-N-methyl-4aH-fluoren-4a-amine,
1,4,9,9a-tetrahydro-3-methyl-N-ethyl-4aH-fluoren-4a-amine,
N-ethyl-1,2,3,4,9,9a-hexahydro-4aH-fluoren-4a-amine,
1,2,3,4,9,9a-hexahydro-N,N-dimethyl-4aH-fluoren-4a-amine,
N-ethyl-1,2,3,4,9,9a-hexahydro-4aH-fluoren-4a-amine,
1,2,3,4,9,9a-hexahydro-N-propyl-4aH-fluoren-4a-amine,
1,2,3,4,9,9a-hexahydro-2,3-dimethyl-N-methyl-4aH-fluoren-4a-amine,
6,7,8,9-tetrahydro-9a(5aH)-dibenzofuranamine,
6,7,8,9-tetrahydro-N-methyl-9a(5aH)-dibenzofuranamine,
N-ethyl-6,7,8,9-tetrahydro-N-methyl-9a(5aH)-dibenzofuranamine,
6,7,8,9-tetrahydro-N-propyl-9a(5aH)-dibenzofuranamine,
6,7,8,9-tetrahydro-N-(methoxypropyl)-9a(5aH)-dibenzofuranamine,
N-ethyl-6,7,8,9-tetrahydro-N-methyl-9a(5aH)-dibenzothiophenamine,
6,9-dihydro-N-methyl-9a(5aH)-dibenzothiophenamine,
6,9-dihydro-N,N-dimethyl-9a(5aH)-dibenzothiophenamine,
2,5,6,7,8,9-hexahydro-N-methyl-4bH-fluoreno[2,3-d]-1,3-dioxole-4b-amine, and
N-ethyl-2,5,6,7,8,9-hexahydro-4bH-fluoreno[2,3-d]-1,3-dioxole-4b-amine.

Especially preferred compounds of the instant invention are:
N-ethyl-6,7,8,9-tetrahydro-9a(5aH)-dibenzofuranamine,
6,7,8,9-tetrahydro-N-methyl-9a(5aH)-dibenzothiophenamine,
1,2,3,4,9,9a-hexahydro-4aH-fluoren-4a-amine,
1,2,3,4,9,9a-hexahydro-N-methyl-4aH-fluoren-4a-amine,
1,2,3,4,9,9a-hexahydro-N-(3-methoxypropyl)-4aH-fluoren-4a-amine, and 1,2,3,4,9,9a-hexahydro-3-methyl-N-methyl-(4aH)-fluoren-4a-amine.

Also included is a method of administering the compounds.

A method of using the compounds as analgesics is also included.

DETAILED DESCRIPTION

The present invention provides for a method of treating neurodegenerative disorders by administering a pharmaceutically effective dose of a compound of formula

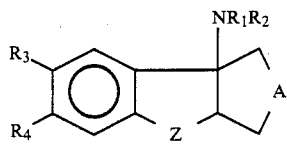

I or a pharmaceutically acceptable acid addition salt thereof
wherein:
Z is methylene, oxygen, or sulfur;
$R_1$ is hydrogen, lower alkyl, or lower alkoxyalkyl;
$R_2$ is hydrogen or lower alkyl;
$R_3$ and $R_4$ are each independently hydrogen or when taken together are methylenedioxy;
A is —$CH_2CH_2$—, —CH=CH— or when Z is methylene A is —CMe=CMe—, —CHMeCHMe—, —CHMeCH$_2$—, —CMe=CH—, —CH$_2$CH$_2$—, or —CH=CH—.

Compounds were prepared using the general routes outlined in the patents referenced above and in *J. Org. Chem.*, 28, 1112, (1963).

The term alkyl, except where otherwise stated, in alkyl per se or in alkoxyalkyl is a straight or branched chain of from one to six carbon atoms.

The term alkoxyalkyl is selected from among alkoxy radicals containing not more than six carbon atoms and includes but is not limited to methoxy, ethoxy, propyloxy, and the like.

The preferred compounds are those of formula I wherein:
Z is methylene or sulfur;
$R_1$ is hydrogen, methyl, ethyl, propyl, or $(CH_2)_3OMe$;
$R_2$ is hydrogen or methyl; and
A is —$CH_2CH_2$—, —CH=CH— or when Z is methylene, A is —CMe=CMe—, —CHMeCHMe—, —CHMeCH$_2$—, —CMe=CH—, —CH$_2$CH$_2$—, or —CH=CH—.

Table I below provides an easy reference for examples of the invention

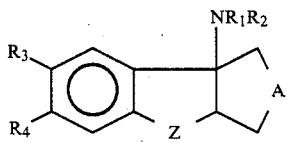

I

TABLE I

| Example | $R_1$ | $R_2$ | $R_3$ | $R_4$ | Z | A |
|---|---|---|---|---|---|---|
| 1 | H | H | H | H | $CH_2$ | $CH_2CH_2$ |
| 2 | Me | H | H | H | $CH_2$ | $CH_2CH_2$ |
| 3 | Me | Me | H | H | $CH_2$ | $CH_2CH_2$ |
| 4 | Et | H | H | H | $CH_2$ | $CH_2CH_2$ |
| 5 | nPr | H | H | H | $CH_2$ | $CH_2CH_2$ |

TABLE I-continued

| Example | $R_1$ | $R_2$ | $R_3$ | $R_4$ | Z | A |
|---|---|---|---|---|---|---|
| 7 | $(CH_2)_4Me$ | H | H | H | $CH_2$ | $CH_2CH_2$ |
| 8 | $(CH_2)_3OMe$ | H | H | H | $CH_2$ | $CH_2CH_2$ |
| 9 | Me | H | —$OCH_2O$— | | $CH_2$ | $CH_2CH_2$ |
| 10 | Et | H | —$OCH_2O$— | | $CH_2$ | $CH_2CH_2$ |
| 11 | $(CH_2)_3OMe$ | H | —$OCH_2O$— | | $CH_2$ | $CH_2CH_2$ |
| 12 | Me | H | H | H | $CH_2$ | $CH(Me)CH_2$ |
| 13 | Me | H | H | H | $CH_2$ | CHMeCHMe |
| 14 | nPr | H | H | H | $CH_2$ | CHMeCHMe |
| 15 | H | H | H | H | $CH_2$ | CH=CH |
| 16 | Me | H | H | H | $CH_2$ | CH=CH |
| 17 | Me | Me | H | H | $CH_2$ | CH=CH |
| 18 | Et | H | H | H | $CH_2$ | CH=CH |
| 19 | nPr | H | H | H | $CH_2$ | CH=CH |
| 20 | H | H | H | H | $CH_2$ | CMe=CMe |
| 21 | Me | H | H | H | $CH_2$ | CMe=CMe |
| 22 | Me | Me | H | H | $CH_2$ | CMe=CMe |
| 23 | Et | H | H | H | $CH_2$ | CMe=CMe |
| 24 | nPr | H | H | H | $CH_2$ | CMe=CMe |
| 25 | Me | H | H | H | O | $CH_2CH_2$ |
| 26 | Me | Et | H | H | O | $CH_2CH_2$ |
| 27 | Et | H | H | H | O | $CH_2CH_2$ |
| 28 | nPr | H | H | H | O | $CH_2CH_2$ |
| 29 | $(CH_2)_3OMe$ | H | H | H | O | $CH_2CH_2$ |
| 30 | Me | H | H | H | S | $CH_2CH_2$ |
| 31 | Me | Et | H | H | S | $CH_2CH_2$ |
| 32 | Me | H | H | H | S | CH=CH |
| 33 | Me | Me | H | H | S | CH=CH |
| 34 | Me | Et | H | H | S | CH=CH |

Compounds of the instant invention include solvates, hydrates, and salts of the compounds of formula I above.

A compound of formula I above is useful both in the free base form and in the form of acid addition salts and both forms are within the scope of the invention. The term pharmaceutically acceptable acid addition salt is intended to mean relatively nontoxic acid addition salts from either inorganic or organic acids such as, for example, hydrochloric, hydrobromic, sulfuric, phosphoric, citric, oxalic, malonic, acetic, maleic, salicylic, ethanesulfonic, malic, gluconic, fumaric, succinic, ascorbic, methanesulfonic, benzenesulfonic, p-toluenesulfonic, and the like as would occur to one skilled in the art.

The acid addition salts of the basic compounds are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

In applications of this invention, the compounds can be used either as free bases or in the form of acid addition salts. The acid addition salts are preferred where greater water solubility is desired.

The compounds used in the invention may contain asymmetric carbon atoms. This invention includes the use of individual enantiomers, diastereomers, or mixtures thereof, which may be prepared or isolated by methods known in the art.

The compounds of the instant invention may be administered in any convenient or effective method for introducing foreign substances into the blood stream of mammals such as by oral, rectal, or parenteral routes. The effective dosage level is for example 0.01 to 50 mg/kg, preferably about 0.05 to 10 mk/kg and especially about 0.05 to 0.5 mg/kg/day and may be administered on a regimen of 1 to 4 times per day.

The pharmaceutical formulations comprising the NMDA receptor antagonists of this invention may be conveniently tablets, pills, capsules, powders, or granules for oral administration; sterile parenteral solutions or suspensions for parenteral administration; or as suppositories for rectal administration.

The compounds useful in the novel method of treatment of this invention bind with a high affinity and displace [$^3$H]-1-[(2-thienyl)cyclohexyl]-piperidine([$^3$H]TCP) from membranes of the rat brain cortex in a reversible and saturable manner. In addition, these useful compounds also inhibit hypoxia and glutamate stimulated influx of calcium into cultured rat cortical neurons.

PHARMACOLOGY

The ability of the compounds of the instant invention to interact with phencyclidene (PCP) receptors is shown in Table II. Tritiated TCP binding, designated RBS1, was carried out essentially as described in *J. Pharmacol. Exp. Ther.*, 238, 739–748 (1986).

The ability of the compounds of the instant invention to inhibit the glutamate and hypoxia stimulated influx of calcium into cultured rat cortical neurons is shown in Table III and Table IV respectively. The methodology for determining the ability of the compounds of the instant invention to inhibit the glutamate stimulated calcium influx (GCI) into cultured rat cortical neurons is to be found in: A. W. Probert and F. W. Marcoux, *Soc. Neurosci. Abstr.*, 13, Part II, 754, (1987). Using a similar culture system, the ability of the compounds of the instant invention to inhibit the hypoxia stimulated influx of calcium (HCI) was determined by incubating cultured cells in an atmosphere of nitrogen (95%) and CO$_2$ (5%) at 37° C. for a period of 4 hours. Calcium influx was determined by subtraction of the stimulated influx in the presence of tetrodotoxin (3 μM) and magnesium (10 mM) from that found in the absence (control) and in the presence of the test substance.

TABLE II

| | Inhibition of [$^3$H]TCP Receptor Binding | | | | | |
|---|---|---|---|---|---|---|
| Example | R$_1$ | R$_2$ | R$_3$ | R$_4$ | Z | A | RBS1 IC$_{50}$ |
| 1 | H | H | H | H | CH$_2$ | CH$_2$CH$_2$ | 27 nM |
| 2 | Me | H | H | H | CH$_2$ | CH$_2$CH$_2$ | 15 nM |
| 8 | (CH$_2$)$_3$OMe | H | H | H | CH$_2$ | CH$_2$CH$_2$ | 102 nM |
| 12 | Me | H | H | H | CH$_2$ | CH(Me)CH$_2$ | 95 nM |
| 27 | Et | H | H | H | O | CH$_2$CH$_2$ | 141 nM |
| 30 | Me | H | H | H | S | CH$_2$CH$_2$ | 10 nM |
| — | PCP | — | | | (reference standard) | — | 40 nM |
| — | TCP | — | | | (reference standard) | — | 9 nM |
| — | ketamine | — | | | (reference standard) | — | 860 nM |
| — | MK-801 | — | | | (reference standard) | — | 3 nM |

As can be seen in the above table (Table II), examples 1, 2, 8, 12, 27 and 30 are potent inhibitors of [$^3$H]TCP receptor binding and as such, are potent noncompetitive NMDA receptor antagonists. In particular, examples 1, 2 and 30 exhibit a potency comparable to both TCP and MK-801, the most potent noncompetitive NMDA antagonist reported to date.

TABLE III

| | Inhibition of Glutamate Stimulated [$^{45}$Ca] Influx (GCI) | | | | | |
|---|---|---|---|---|---|---|
| Example | R$_1$ | R$_2$ | R$_3$ | R$_4$ | Z | A | GCI IC$_{50}$ |
| 1 | H | H | H | H | CH$_2$ | CH$_2$CH$_2$ | |
| 2 | Me | H | H | H | CH$_2$ | CH$_2$CH$_2$ | 304 nM |
| 8 | (CH$_2$)$_3$OMe | H | H | H | CH$_2$ | CH$_2$CH$_2$ | 1900 nM |
| 12 | Me | H | H | H | CH$_2$ | CH(Me)CH$_2$ | 1900 nM |
| 27 | Et | H | H | H | O | CH$_2$CH$_2$ | 1800 nM |
| 30 | Me | H | H | H | S | CH$_2$CH$_2$ | 260 nM |
| — | PCP | — | | | (reference standard) | — | 160 nM |
| — | ketamine | — | | | (reference standard) | — | 5500 nM |
| — | MK-801 | — | | | (reference standard) | — | 51 nM |

As can be seen in the above table (Table III), examples 2, 8, 12, 27 and 30 inhibit the glutamate stimulated influx of calcium into cultured cortical neurons. In particular examples 2 and 30 exhibited similar activity to MK-801. Since glutamate stimulated influx of calcium into neurons has been postulated to be the critical factor in neuronal cell death, the compounds of the instant invention would exhibit a neuroprotective action.

TABLE IV

| | Inhibition of Hypoxia Induced [$^{45}$Ca] Influx (HCI) | | | | | |
|---|---|---|---|---|---|---|
| Example | R$_1$ | R$_2$ | R$_3$ | R$_4$ | Z | A | HCI IC$_{50}$ |
| 1 | H | H | H | H | CH$_2$ | CH$_2$CH$_2$ | 167 nM |
| 2 | Me | H | H | H | CH$_2$ | CH$_2$CH$_2$ | 5 nM |
| 8 | (CH$_2$)$_3$OMe | H | H | H | CH$_2$ | CH$_2$CH$_2$ | 43 nM |
| 12 | Me | H | H | H | CH$_2$ | CH(Me)CH$_2$ | 95 nM |
| 27 | Et | H | H | H | O | CH$_2$CH$_2$ | 124 nM |
| 30 | Me | H | H | H | S | CH$_2$CH$_2$ | 200 nM |
| — | PCP | — | | | (reference standard) | — | 45 nM |
| — | ketamine | — | | | (reference standard) | — | 1900 nM |
| — | MK-801 | — | | | (reference standard) | — | 34 nM |

As can be seen in the above table (Table IV), examples 1, 2, 8, 12, 27 and 30 are potent inhibitors of hypoxia induced calcium influx into cultured neurons. It is believed that the cerebral damage resulting from ischemic, hypoxic, hypoglycemic and other related cerebrovascular disorders results in the release of excess glutamic and aspartic acids from endogenous neuronal stores. The result of such release is the pathologic influx of calcium into neurons and subsequent cell death. The data provided in this table further strongly supports the use of the compounds of the instant invention as effective therapeutic agents for the treatment of stroke and related cerebrovascular disorders.

We claim:

1. A method for treating cerebrovascular disorders which comprises administering to a patient a therapeutically effective amount of a compound of the formula

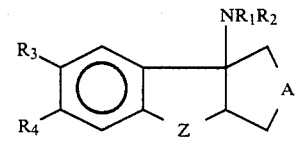

I or a pharmaceutically acceptable acid addition salt thereof wherein:

Z is methylene, oxygen, or sulfur;

$R_1$ is hydrogen, lower alkyl, or lower alkoxyalkyl;
$R_2$ is hydrogen or lower alkyl;
$R_3$ and $R_4$ are each independently hydrogen or when taken together are methylenedioxy;
A is —CH$_2$CH$_2$—, —CH=CH— or when Z is methylene A is —CMe=CMe—, —CHMeCHMe—, —CHMeCH$_2$—, —CMe=CH—, —CH$_2$CH$_2$—, or —CH=CH—.

2. A method for treating cerebrovascular disorders according to claim 1 wherein in a compound of formula I:
Z is methylene or sulfur,
$R_1$ is hydrogen, methyl, ethyl, propyl, or (CH$_2$)$_3$OMe,
$R_2$ is hydrogen or methyl, and
A is —CH$_2$CH$_2$—, —CH=CH— or when Z is methylene A is also —CH(Me)CH$_2$—.

3. A method for treating cerebrovascular disorders according to claim 1 wherein the compound is selected from the group consisting of:
1,4,9,9a-tetrahydro-4aH-fluoren-4a-amine,
1,4,9,9a-tetrahydro-N-methyl-4aH-fluoren-4a-amine,
1,4,9,9a-tetrahydro-N,N-dimethyl-4aH-fluoren-4a-amine,
N-ethyl-1,4,9,9a-tetrahydro-4aH-fluoren-4a-amine,
1,4,9,9a-tetrahydro-N-propyl-4aH-fluoren-4a-amine,
N-butyl-1,4,9,9a-tetrahydro-4aH-fluoren-4a-amine,
1,4,9,9a-tetrahydro-N-pentyl-4aH-fluoren-4a-amine,
1,4,9,9a-tetrahydro-3-methyl-4aH-fluoren-4a-amine,
1,4,9,9a-tetrahydro-3-methyl-N-methyl-4aH-fluoren-4a-amine,
1,4,9,9a-tetrahydro-3-methyl-N-ethyl-4aH-fluoren-4a-amine,
N-ethyl-1,2,3,4,9,9a-hexahydro-4aH-fluoren-4a-amine,
1,2,3,4,9,9a-hexahydro-N,N-dimethyl-4aH-fluoren-4a-amine,
N-ethyl-1,2,3,4,9,9a-hexahydro-4aH-fluoren-4a-amine,
1,2,3,4,9,9a-hexahydro-N-propyl-4aH-fluoren-4a-amine,
1,2,3,4,9,9a-hexahydro-2,3-dimethyl-N-methyl-4aH-fluoren-4a-amine,
6,7,8,9-tetrahydro-9a(5aH)-dibenzofuranamine,
6,7,8,9-tetrahydro-N-methyl-9a(5aH)-dibenzofuranamine,
N-ethyl-6,7,8,9-tetrahydro-N-methyl-9a(5aH)-dibenzofuranamine,
6,7,8,9-tetrahydro-N-propyl-9a(5aH)-dibenzofuranamine,
6,7,8,9-tetrahydro-N-(methoxypropyl)-9a(5aH)-dibenzofuranamine,
N-ethyl-6,7,8,9-tetrahydro-N-methyl-9a(5aH)-dibenzothiophenamine,
6,9-dihydro-N-methyl-9a-(5aH)-dibenzothiophenamine,
6,9-dihydro-N,N-dimethyl-9a-(5aH)-dibenzothiophenamine,
2,5,6,7,8,9-hexahydro-N-methyl-4bH-fluoreno[2,3-d]-1,3-dioxole-4b-amine, and
N-ethyl-2,5,6,7,8,9-hexahydro-4bH-fluoreno[2,3-d]-1,3-dioxole-4b-amine.

4. A method according to claim 1 wherein the compound is:
N-ethyl-6,7,8,9-tetrahydro-9a(5aH)-dibenzofuranamine.

5. A method according to claim 1 wherein the compound is:
6,7,8,9-tetrahydro-N-methyl-9a(5aH)-dibenzothiophenamine.

6. A method according to claim 1 wherein the compound is:
1,2,3,4,9,9a-hexahydro-4aH-fluoren-4a-amine.

7. A method according to claim 1 wherein the compound is:
1,2,3,4,9,9a-hexahydro-N-(3-methoxypropyl)-4aH-fluoren-4a-amine.

8. A method according to claim 1 wherein the compound is:
1,2,3,4,9,9a-hexahydro-N-methyl-4aH-fluoren-4a-amine.

9. A method according to claim 1 wherein the compound is:
1,2,3,4,9,9a-hexahydro-3-methyl-N-methyl-4aH-fluoren-4a-amine.

10. A method according to claim 1 wherein 0.01 to 50 mg/kg by weight of a compound or pharmaceuticaly acceptable salt thereof is administered to a patient.

11. A method of using as an analgesic a compound of formula or a pharmaceutically acceptable acid addition salt thereof wherein:
Z is methylene, oxygen, or sulfur;
$R_1$ is hydrogen, lower alkyl, or lower alkoxyalkyl;
$R_2$ is hydrogen or lower alkyl;
$R_3$ and $R_4$ are each independently hydrogen or when taken together are methylenedioxy;
A is —CH$_2$CH$_2$—, —CH=CH— or when Z is methylene A is —CMe=CMe—, —CHMeCHMe—, —CHMeCH$_2$—, —CMe=CH—, —CH$_2$CH$_2$—, or —CH=CH—.

* * * * *